United States Patent [19]

Preuss et al.

[11] Patent Number: 4,535,074
[45] Date of Patent: Aug. 13, 1985

[54] FUNGICIDAL PHOSPHORYLATED AZOLYL DERIVATIVES

[75] Inventors: Reinhard Preuss; Hermann Perrey, both of Krefeld; Helmut Ritter, Wuppertal; Paul Reinecke, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 593,323

[22] Filed: Mar. 26, 1984

[30] Foreign Application Priority Data

Apr. 15, 1983 [DE] Fed. Rep. of Germany ....... 3313719

[51] Int. Cl.³ .......................... A01N 57/24; C07F 9/65
[52] U.S. Cl. ........................................ 514/93; 514/94; 548/112
[58] Field of Search .......................... 548/112; 424/200

[56] References Cited

FOREIGN PATENT DOCUMENTS 0015387 9/1980 European Pat. Off. .
2600799 7/1977 Fed. Rep. of Germany .
3046329 7/1982 Fed. Rep. of Germany .

Primary Examiner—Richard L. Raymond
Attorney, Agent, or Firm—Sprung, Horn, Kramer & Woods

[57] ABSTRACT

Fungicidally active novel phosphorylated azolyl derivatives of the formula

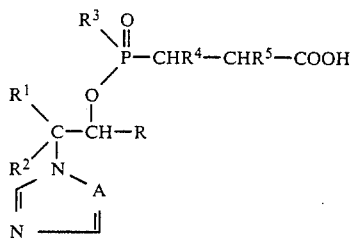

in which
A represents a nitrogen atom or the CH group,
R represents optionally substituted phenyl or the grouping

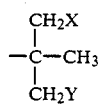

wherein X and Y are identical or different and represent hydrogen or halogen,
$R^1$ represents hydrogen and
$R^2$ represents hydrogen, optionally substituted phenoxy or optionally substituted benzyl, or
$R^1$ and $R^2$ together represent the grouping =CH—Z, wherein Z represents optionally substituted cycloalkyl or optionally substituted phenyl,
$R^3$ represents alkyl, optionally substituted phenyl or optionally substituted benzyl,
$R^4$ represents hydrogen or alkyl and
$R^5$ represents hydrogen or alkyl,
or salts or addition products thereof with metal salts.

8 Claims, No Drawings

FUNGICIDAL PHOSPHORYLATED AZOLYL DERIVATIVES

The present invention relates to new phosphorylated azolyl derivatives, a process for their preparation and their use as fungicides.

It has already been disclosed that certain acylated triazolyl derivatives, such as, for example, 1-chlorophenoxy-3,3-dimethyl-2-ethylcarbonyloxy- or -2-acetoxy- or -2-phenoxyacetoxy-1-(1,2,4-triazol-1-yl)butane or 3-acetoxy-1-cyclohexyl-4,4-dimethyl-2-(1,2,4-triazol-1-yl)-1-pentene, have good fungicidal properties (compare U.S. Pat. No. 4,145,428 and European Pat. No. 0,015,387). However, the action of these compounds is not always completely satisfactory, especially when low amounts and concentrations are applied.

New phosphorylated azolyl derivatives of the general formula

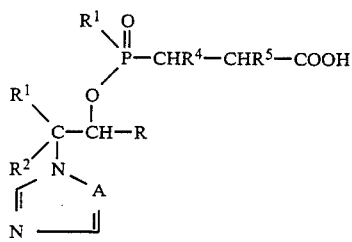  (I)

in which

A represents a nitrogen atom or the CH group,

R represents optionally substituted phenyl or the grouping

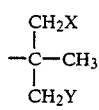

wherein

X and Y are identical or different and represent hydrogen or halogen, $R^1$ represents hydrogen and $R^2$ represents hydrogen, optionally substituted phenoxy or optionally substituted benzyl, or $R^1$ and $R^2$ together represent the grouping =CH—Z, wherein Z represents optionally substituted cycloalkyl or optionally substituted phenyl, $R^3$ represents alkyl, optionally substituted phenyl or optionally substituted benzyl, $R^4$ represents hydrogen or alkyl and $R^5$ represents hydrogen or alkyl, have been found.

Where relevant, depending on their substitution, the compounds of the formula (I) can exist in the form of various geometric isomers (threo- adn erythro-form or E- and Z-form) and in the form of optical isomers; they are chiefly obtained as mixtures.

It has furthermore been found that the phosphorylated azolyl derivatives of the general formula (I) are obtained by a process in which the hydroxyazolyl derivatives of the formula

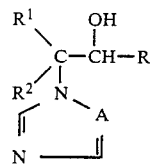  (II)

in which A, $R^1$, $R^2$ and R have the abovementioned meaning, are reacted with 2,5-dioxo-1-oxa-2-phospholanes of the formula

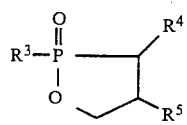  (III)

in which $R^3$, $R^4$ and $R^5$ have the abovementioned meaning, in the presence of a base and if appropriate in the presence of a diluent.

Surprisingly, the compounds of the formula (I) according to the invention exhibit a better fungicidal activity than the acylated triazolyl derivatives known from the prior art, that is to say 1-chlorophenoxy-3,3-dimethyl-2-ethylcarbonyloxy- or -2-acetoxy- or -2-phenoxyacetoxy-1-(1,2,4-triazol-1-yl)-butane or 3-acetoxy-1-cyclohexyl-4,4-dimethyl-2-(1,2,4-triazol-1-yl)-1-pentene, which are closely related compounds structurally and from the point of view of their action. The active compounds according to the invention thus represent an enrichment of the art.

Formula (I) provides a general definition of the phosphorylated azolyl derivatives according to the invention. Preferably, in this formula, A represents a nitrogen atom or the CH group;

R represents phenyl which is optionally mono-, di- or tri-substituted by identical or different substituents from the group comprising halogen and alkyl with 1 to 4 carbon atoms, or represents the grouping

wherein

X and Y are identical or different and represent hydrogen, fluorine or chlorine;

$R^1$ represents hydrogen and $R^2$ represents hydrogen or phenoxy or benzyl, each of which is optionally mono-, di- or tri-substituted by identical or different substituents, substituents which may be mentioned being: halogen, alkyl with 1 to 4 carbon atoms, alkoxycarbonyl with 1 to 4 carbon atoms in the alkyl part, nitro, and optionally halogen-substituted phenyl; or $R^1$ and $R^2$ together represent the grouping =CH—Z, wherein Z represents cycloalkyl which has 5 to 7 carbon atoms and is optionally mono-, di- or tri-substituted by identical or different substituents, substituents which may be mentioned being alkyl with 1 to 4 carbon atoms and halogen; or represents phenyl which is optionally mono-, di- or tri-substituted by identical or different substituents, substituents which may be mentioned being: halogen, alkyl with 1 to 4 carbon atoms, and haloalkyl with 1 to 2 carbon atoms and 1 to 5 identical or different halogen atoms, such as fluorine and chlorine atoms;

R³ represents alkyl with 1 to 4 carbon atoms, or phenyl or benzyl, each of which is optionally mono-, di- or tri-substituted by identical or different substituents, possible substituents being the substituents on phenyl which have already been mentioned under Z;

R⁴ represents hydrogen or alkyl with 1 to 4 carbon atoms and

R⁵ represents hydrogen or alkyl with 1 to 4 carbon atoms.

Particularly preferred compounds of the formula (I) are those in which

A represents a nitrogen atom or the CH group;

R represents phenyl which is optionally mono- or di-substituted by identical or different substituents, or represents the grouping

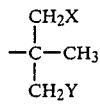

wherein

X and Y are identical or different and represent hydrogen, fluorine or chlorine;

R¹ represents hydrogen and

R² represents hydrogen or phenoxy or benzyl, each of which is optionally mono- or di-substituted by identical or different substituents, substituents which may be mentioned being: fluorine, chlorine, methyl, methoxycarbonyl, ethoxycarbonyl, nitro, phenyl, chlorophenyl and fluorophenyl; or R¹ and R² together represent the grouping =CH—Z, wherein Z represents cyclopentyl or cyclohexyl, each of which is optionally substituted by methyl, or represents phenyl which is optionally mono- or di-substituted by identical or different substituents, substituents which may be mentioned being: fluorine, chlorine, methyl, tert.-butyl and trifluoromethyl;

R³ represents methyl or ethyl, or phenyl or benzyl, each of which is optionally mono- or di-substituted by identical or different substituents, possible substituents being the substituents on phenyl which have already been mentioned for Z;

R⁴ represents hydrogen, methyl or ethyl and

R⁵ represents hydrogen, methyl or ethyl. Very particularly preferred compounds of the formula (I) are those in which A represents a nitrogen atom or the CH group;

R represents phenyl which is mono- or di-substituted by chlorine, or represents the grouping

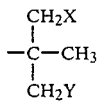

wherein

X and Y are identical or different and represent hydrogen, fluorine or chlorine;

R¹ represents hydrogen and

R² represents hydrogen or phenoxy or benzyl, each of which is optionally mono- or di-substituted by identical or different substituents, substituents which may be mentioned being fluorine, chlorine, methyl and phenyl, or R¹ and R² together represent the grouping =CH—Z, wherein Z represents cyclohexyl, or represents phenyl which is optionally mono- or di-substituted by identical or different substituents, substituents which may be mentioned being chlorine or fluorine;

R³ represents methyl and

R⁴ and R⁵ represent hydrogen.

If, for example, 1-(4-chlorophenoxy)-3,3-dimethyl-1-(1,2,4-triazol-1-yl)-2-butanol and 2-methyl-2,5-dioxo-1-oxa-2-phospholane are used as starting substances, the course of the reaction in the process according to the invention can be represented by the following equation:

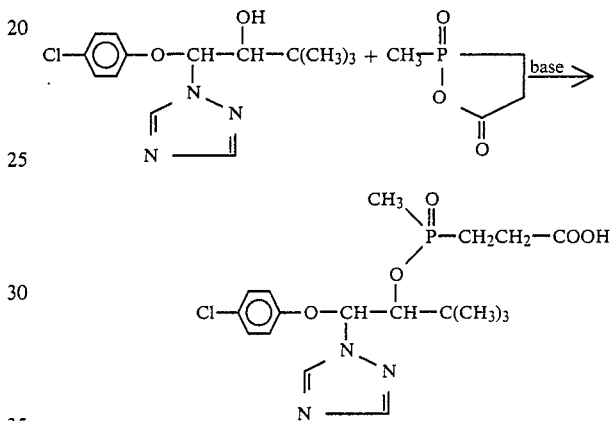

Formula (II) provides a general definition of the hydroxy-azolyl derivatives required as starting substances in carrying out the process according to the invention. In this formula, A, R¹, R², X and Y preferably have those meanings which have already been mentioned as preferred for these radicals in connection with the description of the substances of the formula (I) according to the invention.

The hydroxy-azolyl derivatives of the formula (II) are known (compare, for example, U.S. Pat. Nos. 3,952,002, 3,940,414, U.S. Ser. No. 792,756, filed May 2, 1977, pending, DE-OS(German Published Specification) No. 2,610,022, DE-OS (German Published Specification) No. 2,638,470, U.S. Pat. No. 4,284,639, DE-OS(German Published Specification) No. 2,632,602, U.S. Pat. Nos. 4,207,328, 4,284,639, 4,382,944, U.S. Ser. No. 321,642, filed Nov. 16, 1981, pending and European Patent Nos. 0,015,387 and 0,044,425).

Formula (III) provides a general definition of the 2,5-dioxo-1-oxa-2-phospholanes also to be used as starting substances for the process according to the invention. In this formula, R³, R⁴ and R⁵ preferably have those meanings which have already been mentioned as preferred for these radicals in connection with the description of the substances of the formula (I) according to the invention.

The 2,5-dioxo-1-oxa-2-phospholanes of the formula (III) are likewise known (compare, for example, Z.obsc. Chim. 37, (1967), pages 710–714 and DE-OS (German Published Specification) No. 2,346,787); or they can be obtained by the processes mentioned in these references, by reacting dichlorophosphanes of the formula $$R^3-PCl_2 \quad (IV)$$

in which $R^3$ has the abovementioned meaning,
with unsaturated carboxylic acids of the formula $$CHR^4=CR^5-COOH \quad (V)$$

in which $R^4$ and $R^5$ have the abovementioned meaning, to give the corresponding dichlorides of phosphinic acids, of the formula $$\underset{Cl}{\underset{|}{R^3-\overset{O}{\overset{\|}{P}}-CHR^4-CHR^5-CO-Cl}} \quad (VI)$$

in which $R^3$, $R^4$ and $R^5$ have the abovementioned meanings,
which can then easily be converted into the corresponding cyclic anhydrides of the formula (II) by means of acetic anhydride.

The process according to the invention is preferably carried out in the presence of a base as a catalyst. Preferred bases include organic bases, such as tertiary amines, such as, for example, triethylamine or tributylamine, or such as pyridine.

If appropriate, the process according to the invention is carried out in the presence of a diluent. Preferred diluents include organic solvents which are inert under the reaction conditions, such as, in particular, chlorinated aliphatic hydrocarbons, for example methylene chloride or carbon tetrachloride, or aromatic hydrocarbons, for example benzene or toluene.

The reaction temperatures can be varied within a substantial range in carrying out the process according to the invention. In general, the reaction is carried out between 20° and 150° C., preferably between 25° and 110° C.; if a solvent is used, the reaction is preferably carried out at its boiling point.

In carrying out the process according to the invention, a slight excess (about 10 to 30 mol%) of 2,5-dioxo-1-oxa-2-pholane of the formula (III) and likewise of base is preferably employed per mol of hydroxyazolyl derivative of the formula (II). To isolate the compounds of the formula (I), the solvent is distilled off, if appropriate, and the residue is worked up by customary methods.

If appropriate, a strong acid or a metal salt can be added onto the compounds of the formula (I) in a generally customary and known manner.

Since the compounds of the formula (I) contain a free carboxyl group, it is also possible to obtain salts in a known manner by reaction with bases.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating cereal diseases, such as *Puccinia recondita, Pyrenophora teres, Erysiphe graminis* and *Cochliobolus sativus;* powdery mildew diseases, such as *Podosphaera Leucotricha* and *Sphaerotheca fuligenea;* and rice diseases, such as *Pyricularia oryzae* and *Pellicularia sasakii.*

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts or iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g are generally required.

For the treatment of soil, active compound concentrations of 0.00001 to 0.1% by weight, preferably 0.0001 to 0.02% by weight, are required at the place of action.

PREPARATION EXAMPLES

Example 1

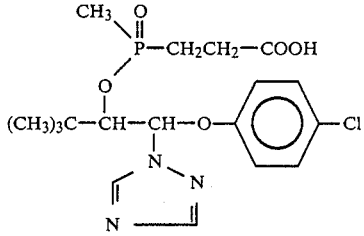

(a)(with solvent)

118.4 g (0.4 mol) of 1-(4-chlorophenoxy)-3,3-dimethyl-1-(1,2,4-triazol-1-yl)-2-butanol, 67 g (0.5 mol) of 2-methyl-2,5-dioxo-1-oxa-2-phospholane and 49.5 g (0.5 mol) of triethylamine are heated under reflux in 1,000 ml of anhydrous methylene chloride, with exclusion of moisture, for 10 hours. The mixture is then concentrated by distilling off the solvent and the residue is dissolved in 10% strength sodium bicarbonate solution. Undissolved constituents are filtered off, the filtrate is brought to pH 3 with 10% strength hydrochloric acid and extracted twice with methylene chloride and the combined organic phases are dried over sodium sulphate, filtered and concentrated in vacuo. 155 g of the above compound of glass-like consistency are obtained.

(b)(without a solvent)

29.6 g (0.1 mol) of 1-(4-chlorophenoxy)-3,3-dimethyl-1-(1,2,4-triazol-1-yl)-2-butanol, 14.7 g (0.11 mol) of 2-methyl-2,5-dioxo-1-oxa-2-phospholane and 10.9 g (0.11 mol) of triethylamine are heated at 90° C. for 10 hours, under a nitrogen atmosphere and with exclusion of moisture. The mixture is allowed to cool, the reaction mixture is dissolved in 10% strength sodium bicarbonate solution, undissolved constituents are filtered off and the filtrate is brought to pH 3 with 10% strength hydrochloric acid. It is then extracted with methylene chloride, dried over sodium sulphate, filtered and concentrated in vacuo. 31 g of the above compound of glass-like consistency are obtained.

The following compounds of the general formula

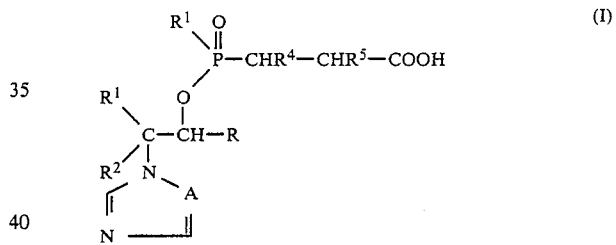

are obtained in a corresponding manner:
the process specified:

| Example No. | R | $R^1$ | $R^2$ | $R^3$ | $R^4$ | $R^5$ | A | Physical constants |
|---|---|---|---|---|---|---|---|---|
| 2 | —C(CH$_3$)$_3$ | H | ⌬—⌬—O— | CH$_3$ | H | H | N | glass-like |
| 3 | —C(CH$_3$)$_3$ | H | ⟨H⟩—CH= | CH$_3$ | H | H | N | glass-like |
| 4 | —C(CH$_3$)$_3$ | H | Cl—⌬(CH$_3$)—O— | CH$_3$ | H | H | N | glass-like |
| 5 | —C(CH$_3$)$_3$ | H | Cl—⌬(Cl)—CH$_2$— | CH$_3$ | H | H | N | glass-like |
| 6 | —C(CH$_3$)$_3$ | H | Cl—⌬—O— | CH$_3$ | H | H | CH | glass-like |

-continued

| Example No. | R | R¹ | R² | R³ | R⁴ | R⁵ | A | Physical constants |
|---|---|---|---|---|---|---|---|---|
| 7 | —C(CH₃)₂CH₂Cl | H | Cl,Cl-C₆H₂(Cl)-O— | CH₃ | H | H | CH | glass-like |
| 8 | —C(CH₃)₂CH₂F | H | Cl,Cl-C₆H₂(Cl)-O— | CH₃ | H | H | CH | glass-like |
| 9 | —C(CH₃)₃ | H | Cl-C₆H₄-CH₂— | CH₃ | H | H | N | glass-like |
| 10 | —C(CH₃)₂CH₃F | H | Cl-C₆H₃(Cl)-O— | CH₃ | H | H | N | glass-like |
| 11 | —C(CH₃)₂CH₂Cl | H | Cl-C₆H₄-O— | CH₃ | H | H | N | glass-like |
| 12 | —C(CH₃)₂CH₂Cl | H | C₆H₅-O— | CH₃ | H | H | N | glass-like |
| 13 | Cl,Cl-C₆H₃— | H | Cl-C₆H₄-O— | CH₃ | H | H | CH | glass-like |

With regard to the above-indicated examples the following characteristic spectroscopic data are given:

Example 1:
¹H-NMR: δ=9.25 CO₂H, 1H; δ=4.9–4.7 POCR₂H, 1H.
IR: ν=3500–2800 cm⁻¹ CO₂H; ν=1250 cm⁻¹, R₃PO.

Example 2:
IR ν=3400 cm⁻¹, CO₂H; ν=1720 cm⁻¹, C=O; ν=1230 cm⁻¹, R₃PO.
¹H-NMR δ=10.2 ppm CO₂H; δ=5.0–4.75 ppm POCR₂H.

Example 3:
IR ν=3400 cm⁻¹, CO₂H; ν=1720 cm⁻¹, C=O; ν=1200 cm⁻¹, R₃PO.

Example 5:
IR ν=3400 cm⁻¹, CO₂H; ν=1720 cm⁻¹, C=O; ν=1200 cm⁻¹, R₃PO.
¹H-NMR δ=4.65–4.3 ppm POCR₂H; δ=1.8–1.55 ppm R₃P—CH₃.

USE EXAMPLES

The compounds shown below are employed as comparison substances in the use examples which follow:

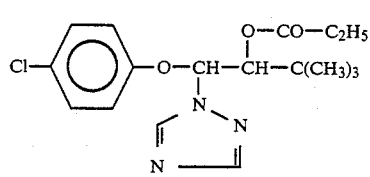
(A)

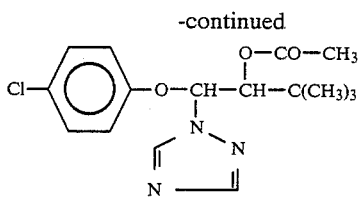
(B)

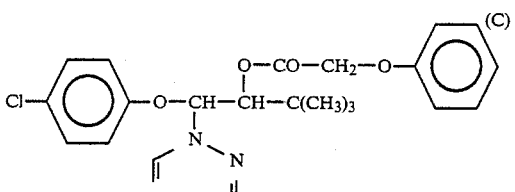
(C)

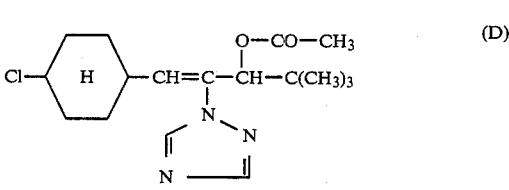
(D)

EXAMPLE A

Puccinia test (wheat)/protective

Solvent: 100 parts by weight of dimethylformamide
Emulsifer: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are inoculated with a spore suspension of *Puccinia recondita* in a 0.1% strength aqueous agar solution. After the spore suspension has dried on, the plants are sprayed with the preparation of active compound until dew-moist. The plants remain in an incubation cabinet at 20° C. and 100% relative atmospheric humidity for 24 hours.

The plants are placed in a greenhouse at a temperature of about 20° C. and a relative atmospheric humidity of about 80% in order to promote the development of rust pustules.

Evaluation is carried out 10 days after the inoculation.

In this test, a clearly superior activity compared with the prior art is shown, for example, by the compound according to the following preparation example: 1.

EXAMPLE B

Pyrenophora teres test (barley)/protective

Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dewmoist. After the spray coating has dried on, the plants are sprayed with a conidia suspension of *Pyrenophora teres*. The plants then remain in an incubation cabinet at 20° C. and 100% relative atmospheric humidity for 48 hours.

The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compound according to the following preparation example: 3.

EXAMPLE C

Podosphaera test (apple)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated by dusting with conidia of the powdery mildew of apple causative organism (*Podosphaera leucotricha*).

The plants are then placed in a greenhouse at 23° C. and a relative atmospheric humidity of about 70%.

Evaluation is carried out 9 days after the inoculation.

In this test, a clearly superior activity compared with the prior art is shown, for example, by the compounds according to the following preparation example: 1.

EXAMPLE D

Sphaerotheca test (cucumber)/protective

Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Sphaerotheca fuliginea*.

The plants are then placed in a greenhouse at 23° to 24° C. and at a relative atmospheric humidity of about 75%.

Evaluation is carried out 10 days after the inoculation.

In this test, a clearly superior activity compared with the prior art is shown, for example, by the compound according to the following preparation example: 1.

It will be appreciated that the instant specification and examples are set forth by way of illustration and not limitation, and that various modifications and changes may be made without departing from the spirit and scope of the present invention.

We claim:

1. A phosphorylated azolyl derivative of the formula

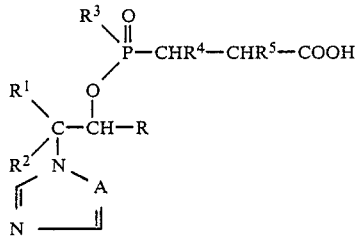

in which

A represents a nitrogen atom or the CH group,

R represents phenyl which is optionally mono-, di- or tri-substituted by identical or different substituents from the group comprising halogen and alkyl with 1 to 4 carbon atoms, or represents the grouping

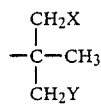

wherein X and Y are identical or different and represent hydrogen, fluorine or chlorine;

$R^1$ represents hydrogen and $R^2$ represents hydrogen or phenoxy or benzyl, each of which is optionally mono-, di- or tri-substituted by identical or different substituents from the group comprising halogen, alkyl with 1 to 4 carbon atoms, alkoxycarbonyl with 1 to 4 carbon atoms in the alkyl part, nitro and optionally halogen-substituted phenyl, or $R^1$ and $R^2$ together represent the grouping =CH—Z, wherein Z represents cycloalkyl which has 5 to 7 carbon atoms and is optionally mono-, di- or tri-substituted by identical or different substituents from the group comprising alkyl with 1 to 4 carbon atoms and halogen, or represents phenyl which is optionally mono-, di- or tri-substituted by identical or different substituents from the group comprising halogen, alkyl with 1 to 4 carbon atoms and haloalkyl with 1 to 2 carbon atoms and 1 to 5 identical or different halogen atoms, $R^3$ represents alkyl with 1 to 4 carbon atoms, or phenyl or benzyl, each of which is optionally mono-, di- or tri-substituted by identical or different substituents, possible substituents being the substituents on phenyl which have already been mentioned under Z, $R^4$ represents hydrogen or alkyl with 1 to 4 carbon atoms and $R^5$ represents hydrogen or alkyl with 1 to 4 carbon atoms, or a salt or addition product thereof with a metal salt.

2. A compound, salt or addition product according to claim 1, in which

R represents phenyl which is optionally mono- or di-substituted by identical or different substituents, or represents the grouping $$\begin{array}{c} CH_2X \\ | \\ -C-CH_3 \\ | \\ CH_2Y \end{array}$$

wherein X and Y are identical or different and represent hydrogen, fluorine or chlorine, $R^1$ represents hydrogen and $R^2$ represents hydrogen or phenoxy or benzyl, each of which is optionally mono- or di-substituted by identical or different substituents from the group comprising fluorine, chlorine, methyl, methoxycarbonyl, ethoxycarbonyl, nitro, phenyl, chlorophenyl and fluorophenyl; or $R^1$ and $R^2$ together represent the grouping =CH—Z, wherein Z represents cyclopentyl or cyclohexyl, each of which is optionally substituted by methyl, or represents phenyl which is optionally mono- or di-substituted by identical or different substituents from the group comprising fluorine, chlorine, methyl, tert.-butyl and trifluoromethyl;

$R^3$ represents methyl or ethyl, or phenyl or benzyl, each of which is optionally mono- or di-substituted by identical or different substituents, possible substituents being the substituents on phenyl which have already been mentioned for Z, $R^4$ represents hydrogen, methyl or ethyl and $R^5$ represents hydrogen, methyl or ethyl.

3. A compound according to claim 1 wherein such compound is or a salt or addition product thereof with a metal salt.

4. A compound according to claim 1 wherein such compound is or a salt or addition product thereof with a metal salt.

5. A compound according to claim 1 wherein such compound is or a salt or addition product thereof with a metal salt.

6. A fungicidal composition comprising a fungicidally effective amount of a compound, salt or addition product according to claim 1 in admixture with a diluent.

7. A method of combatting fungi which comprises administering to such fungi or to a fungus habitat a fungicidally effective amount of a compound, salt or addition product according to claim 1.

8. The method according to claim 7, wherein such compound is

UNITED STATES PATENT AND TRADEMARK OFFICE
CERTIFICATE OF CORRECTION

PATENT NO. : 4,535,074
DATED : August 13, 1985
INVENTOR(S) : Reinhard Preuss, et al.

It is certified that error appears in the above-identified patent and that said Letters Patent is hereby corrected as shown below:

Col. 1, line 21 and Col. 8, line 31  Beginning of formula delete "$R^1\diagdown O\atop \diagdown P$" and substitute $--R^3\diagdown O\atop \diagdown P--$ Col. 2, line 20  Delete "$O\diagdown\diagup$" and substitute $--O\diagdown\!\!\!\!\!_O\diagup--$ Col. 7, line 1  Delete "or" and substitute --of--

Signed and Sealed this

Eighth Day of July 1986

[SEAL]

Attest:

DONALD J. QUIGG

Attesting Officer

Commissioner of Patents and Trademarks